United States Patent [19]
Simmons et al.

[11] 3,993,154
[45] Nov. 23, 1976

[54] WHEELCHAIR-MOUNTED CONTROL APPARATUS

[75] Inventors: Alden C. Simmons, Boulder; James T. McFadden, Arvada, both of Colo.; Robert S. Bennett, Towson, Md.

[73] Assignee: Whittaker Corporation, Los Angeles, Calif.

[22] Filed: Nov. 5, 1975

[21] Appl. No.: 629,033

[52] U.S. Cl. .................. 180/77 R; 180/DIG. 3; 180/65 R; 200/DIG. 1; 318/16
[51] Int. Cl.² ........................................ B60K 26/02
[58] Field of Search .................. 180/1 R, 65 R, 6.5, 180/DIG. 3, 77 R; 318/16; 200/DIG. 1, DIG. 2; 297/DIG. 4

[56] References Cited
UNITED STATES PATENTS

| | | | |
|---|---|---|---|
| 3,111,181 | 11/1963 | Yatich | 180/DIG. 3 |
| 3,218,530 | 11/1965 | Momberg | 318/16 |
| 3,374,845 | 3/1968 | Selwyn | 180/6.5 |
| 3,641,410 | 2/1972 | Vogelsberg | 200/DIG. 1 |
| 3,728,501 | 4/1973 | Larson | 200/DIG. 1 |
| 3,787,732 | 1/1974 | Larson | 200/DIG. 1 |

OTHER PUBLICATIONS
"The Eyes Have It" –Electronics & Power, Sept. 1971, vol. 17, p. 361.

*Primary Examiner*—Robert R. Song
*Assistant Examiner*—Terrance L. Siemens
*Attorney, Agent, or Firm*—Henry M. Bissell

[57] ABSTRACT

A wheelchair mounted control system may be activated to enable propelling of the wheelchair at different predetermined speeds, to cause portions of the wheelchair to recline or be elevated, or to cause a signal to be generated to operate other apparatus such as a book page turner, a light switch or a television tuner, merely by positioning the neck or other skin-exposed body portion of a person in the wheelchair who is otherwise largely incapable of movement. Particular structure includes a periodic electric field source and a pair of field pickup elements adapted to be selectively contacted by the skin of a movable portion of the disabled person's body to cause, for example, activation of stepping switches and associated control relays whereby wheelchair drive motor speed is preselected and recline/elevation motor apparatus is activated for effecting the desired control of various adjustable portions of the wheelchair.

14 Claims, 2 Drawing Figures

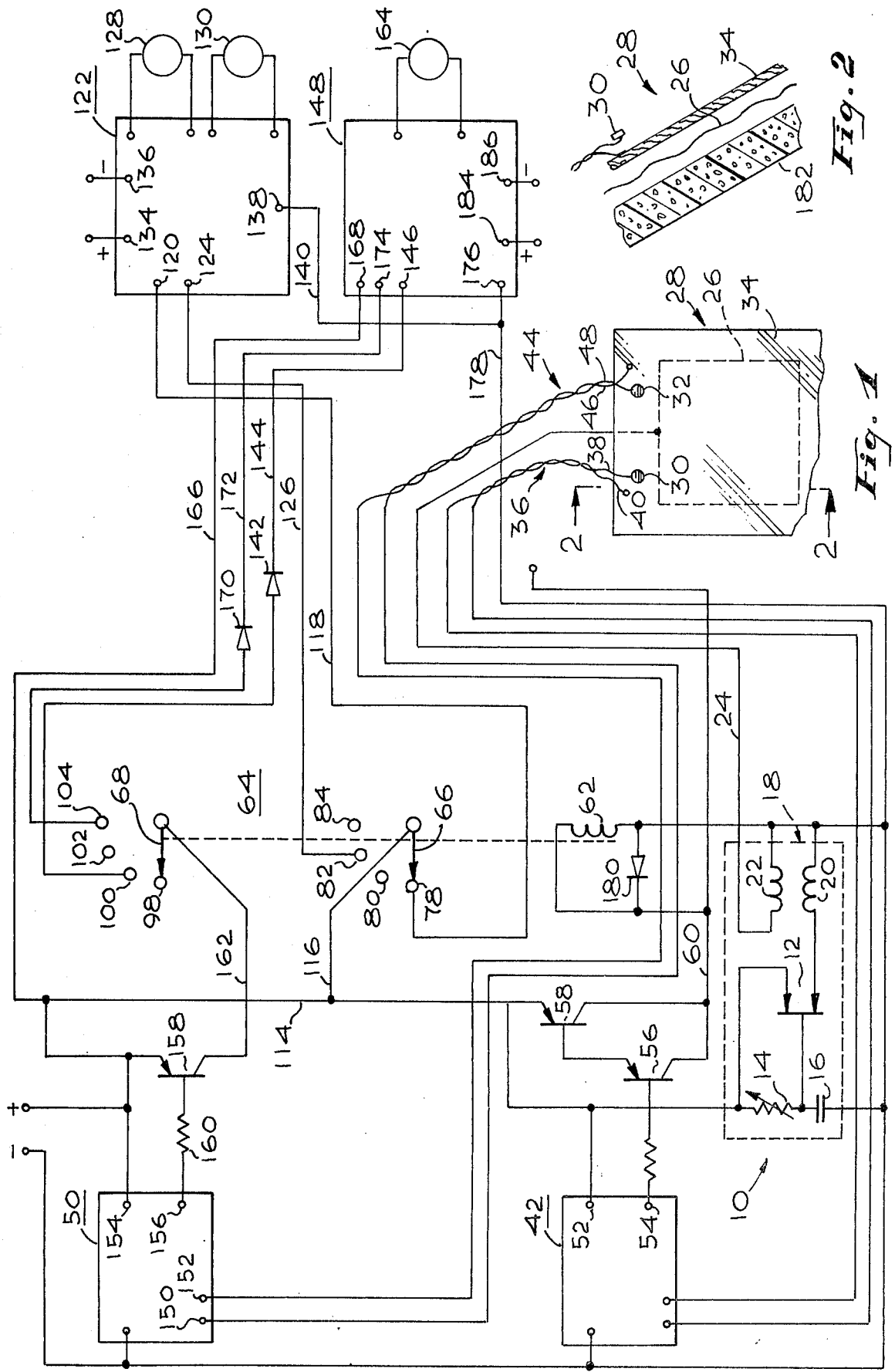

WHEELCHAIR-MOUNTED CONTROL APPARATUS

BACKGROUND OF THE INVENTION

1. Field of the Invention

This invention relates to motorized wheelchairs and, more particularly, to wheelchair-mounted control systems for enabling disabled persons to control operations of a motorized wheelchair, etc. with any movable portion of their body that enables them to put exposed skin into momentary contact with contact elements.

2. Description of the Prior Art

Motorized wheelchairs have been a boon to disabled people. However, for persons who are substantially paralyzed from the neck down, very much weakened or who are quadriplegic, the problem of operating or controlling the motorized wheelchair (or other necessary functions) is formidable. Generally, such persons must have a constant attendant and, because of economics and other practical considerations, the ability of such persons to have any degree of independence and make any contribution to society has been severely limited.

Various mechanisms have been proposed for permitting a quadriplegic to attain some degree of control over movement of a motorized wheelchair. For example, U.S. Pat. No. 3,374,845 of Selwyn provides a head-mounted servo-control system in which the handicapped individual, by a selective movement of his head, can command the operation of a motorized wheelchair. The system disclosed in that patent uses a head-mounted unit, in the form of a helmet or eyeglass frame, containing a position sensing assembly for responding to the different directions of movement of the user's head. Unfortunately, the system disclosed in the Selwyn patent is quite complex and would be very expensive to put into practice. As a result of its complexity, it would also tend to suffer from the maintenance and repair problems naturally associated with complex systems. It seems apparent that to the disabled individual, reliability is the paramount characteristic of any prosthetic or other device he utilizes. However, although cost may be of secondary importance, it is still a significant factor in bringing to the many disabled persons in our society the benefits of modern technology.

Other wheelchair control systems utilize the user's eye movement or reflectivity of the user's eye to effect control and operation; however, such systems are very sensitive to ambient lighting conditions, a strong light often causing the system to "run away". Still other wheelchair control systems employ breath-operated pressure switches or tongue-operated toggle switches; however, such apparatus often require more strength on the part of the user that he can exert.

For these and other reasons, a need still exists for a wheelchair control system which a user, having substantially no strength, can operate.

SUMMARY OF THE INVENTION

The wheelchair-mounted control apparatus, in accordance with the present invention, comprises a wheelchair, a periodic energy field source means mounted on the wheelchair, and an energy field radiating means connected to the source means and positioned in the wheelchair to radiate the energy field from the source means into a wheelchair user's body. A field pickup element is mounted on the wheelchair where it can be selectively and momentarily contacted by a wheelchair user's exposed skin and thereby pick up the energy field from the user's body. Detecting means, connected to the pickup element, provide output signals in response to the energy field picked up by the pickup element. At least one function performing means is mounted on the wheelchair. Controlling means are connected to the function performing means to control the operation thereof in response to the output signals from the detecting means.

More specifically, the function performing means includes wheelchair propelling means and means for moving portions of the wheelchair into user recline and elevate positions. Two drive speeds are provided for motors of the propelling means and recline and elevate modes of operation are provided for the reclining and elevating means. The controlling means includes a stepping switch having a pair of movable contacts which are stepped, in unison, in response to detecting means output signals. Two fixed contacts associated with the first of the movable contacts are connected to the drive motors for selecting either of the two drive speeds. Two fixed contacts associated with the second movable contact are connected to the reclining and elevating means for selecting either of the recline and elevate modes.

Successive output signals from the detecting means causes selection, in sequence, of a first (low) drive speed, the recline mode, a second (high) drive speed and the elevate mode.

When the stepping switch is then trapped into either of the low or high speed positions, the wheelchair can be caused actually to be propelled by conventional controls, such as a "joystick", at a low or high rate of movement.

A second field pickup element is provided for the user's control of the reclining and elevating means after the stepping switch has been stepped into either of the recline or elevate mode positions. A second detecting means is connected to the second pickup element and provides output signals for controlling the extent of movement of the movable portions of the wheelchair by the reclining and elevating means. The reclining or elevating continues, within predetermined limits, as long as the user maintains skin contact with the second pickup.

In this manner, means are provided whereby a wheelchair user having only very limited movement of, for example, his head may, with negligible force, control speeds at which his wheelchair may be propelled, and the manner in which portions of the wheelchair may be moved to allow him to assume reclined or elevated positions. The controlling means are easily adapted for controlling other functions important to the wheelchair user, such as turning pages of a book, turning lights on and off, operating a television set, or signaling an attendant.

BRIEF DESCRIPTION OF THE DRAWINGS

A better understanding of the present invention may be had from a consideration of the following detailed description, taken in conjunction with the accompanying drawings, in which:

FIG. 1 is a drawing partially in block form, partially in schematic form and partially in cutaway form showing a motorized wheelchair control system, according to the present invention; and FIG. 2 is a cross-sectional view taken along line 2—2 in FIG. 1, showing positioning of the conductive foil and skin contact elements.

DESCRIPTION OF THE PREFERRED EMBODIMENT

As shown in FIGS. 1 and 2, a motorized wheelchair drive control system, in accordance with the present invention, includes an oscillator 10 comprising a transistor 12, a variable resistor 14, a capacitor 16 and a transformer 18 having a primary 20 and a secondary 22. Low power signal energy is carried by a conductor 24 to a thin, conductive metal foil 26 located in a backrest portion 28 of a motorized wheelchair, the remainder of which is not shown. Such positioning of the foil 26 can be seen more clearly in FIG. 2. Alternatively, the foil 26 may be located in any other portion of the wheelchair where it will be proximate to major portions of a user's body.

Two conductive metal field pickup or skin-contact elements 30 and 32 are supported in any location on the wheelchair where they may be momentarily contacted at will by any exposed skin portion of the wheelchair user, and are arranged to be separated from each other by a short distance so that they may be individually and selectively contacted. For example, the elements 30 and 32 may be positioned for selective contact by the neck of the wheelchair user. The foil 26 acts as a radiating source of an oscillating or periodic energy or signal field by virtue of being connected through to the oscillator 10, thereby radiating the energy field into the body of an individual sitting in the motorized wheelchair and leaning against the backrest 28. Because of its low power characteristics, this energy field has no deleterious effects upon the person using the wheelchair. Adjustment of the variable resistor 14 causes changing of the frequency of oscillation of the oscillator 10, it having been found that the effectiveness of the person as a receiving antenna for the signal energy from the oscillator 10 can be optimized by such adjustment of oscillator frequency.

When the individual sitting in the motorized wheelchair, and leaning against the backrest 28 to receive radiations from the foil 26, places his neck (or any other exposed skin portion of his body) in contact with the skin-contact element 30, the signal energy from the foil 26 and through the user's body is coupled to a transmission line 36 which comprises a conductor 38 and a conductor 40. The received signal energy is applied through the line 36 to the input of the detector-dc amplifier 42 for processing. Similarly, when the person using the wheelchair places his neck or any other exposed portion of his skin in contact with the skin-contact element 32, a transmission line 44, comprising a conductor 46, connected to such skin-contact element and a conductor 48, secured in proximity to the skin-contact element, carries the signal energy from the skin of the wheelchair user to a detector-dc amplifier 50 where the signal energy is processed. The lines 36 and 44 are formed of twisted pairs of conductors to minimize the pickup of extraneous or spurious signals from adjacent electrical equipment, or from the foil 26 itself.

Amplifiers 42 and 50 may incorporate any of the many forms of circuits, well-known in the art, for detecting signal energy, converting it to direct current signals and amplifying those signals. Such circuits are now generally available in integrated circuit form. For example, an integrated circuit that will perform the functions required for detector-dc amplifiers 42 and 50, respectively, is available from Magic Dot, Inc., Minneapolis, Minn.

Each time the exposed skin of the wheelchair user makes momentary contact with element 30, a dc output pulse appears between a pair of output terminals 52 and 54 of the amplifier 42, the pulse length depending upon how long the skin of the user is maintained in contact with the skin-contact element. The output pulse is amplified by a transistor 56 and a transistor 58 connected in a "Darlington" circuit arrangement, the resulting output dc signal at a conductor 60 being used to drive an acitvating solenoid 62 of two-level stepping or rotary switch 64. The switch 64 has a pair of movable or clockwise (as seen in FIG. 1) rotatable contacts 66 and 68, which turn in unison each time the solenoid 62 receives a dc pulse through the conductor 60. The contact 66 cooperates with four fixed contacts 78, 80, 82 and 84 and the contact 68 cooperates with four fixed contacts 98, 100, 102 and 104. The contacts 66 and 68, which move in unison, are, for the purpose of simplifying the presentation, considered to have the same relative initial positions at contact 78 and 98, respectively, as are shown in FIG. 1.

With the movable contact 66 at fixed contact 78, positive control voltage is applied, by conductor 114, a conductor 116, the movable contact 66, the fixed contact 78 and a conductor 118, to a first "low speed" input control terminal 120 on a drive motor controller 122. When the movable contact 66 has subsequently been stepped twice into contact with the fixed contact 82, positive voltage is applied to a second "high speed" input control terminal 124 on the drive motor controller 122 (through a conductor 126). The circuit of the drive motor controller 122 is conventional and comprises relays and resistors connected in a well-known fashion (such as is shown in U.S. Pat. No. 3,100,860 to Rosenthal) to provide control of current through a left drive motor 128 and a right drive motor 130. Power for the operation of the left and right drive motors 128 and 130, respectively, is derived from power source — usually automobile battery mounted on the wheelchair — (not shown) connected to a pair of input terminals 134 and 136. A control current return path is provided through a terminal 138 and a conductor 140. With the movable contact 66 aligned with the contact 78, the drive motors 128 and 130 are ready to be operated in a "slow speed" (12v) mode by other control means, such as a "joystick" (not shown) which causes power to be supplied to the drive motor and the wheelchair wheels. With the movable contact 66 engaging the fixed contact 82, the drive motors 128 and 130 are ready to be operated in a "high speed" (24v) mode. That is, the movable contact 66 selects the speed at which the wheelchair will be propelled when the "joystick" is operated.

When the movable contact 66 is stepped (by means of the element 30) into contact with the fixed contact 80, the positive voltage appearing on the conductor 116 is supplied to no other part of the circuit since the fixed contact 80 has no external connection. However, because the movable contact 68 is ganged for movement with the contact 66 when the contact 66 is in contact with the fixed contact 80, the contact 68 is in contact with the fixed contact 100, and is thereby coupled, through a protective diode 142 and a conductor 144, to an input terminal 146 on a recline/elevate controller 148.

The user of the wheelchair, having stepped contact 68 to contact 100 (by placing some part of his skin into momentary contact with the element 30), may now move some part of his skin into contact with the contact element 32 to cause a current in the transmission line 44 and the application of a current between a first input terminal 150 and a second input terminal 152 on the amplifier 50. Upon the application of the signal to the terminals 150 and 152, and output dc signal appears across a pair of amplifier output terminals 154 and 156, the amplifier output signal being transmitted to a transistor 158, through a coupling resistor 160, for further amplification. The output signal from the transistor 158 is applied to the movable contact 68 through a conductor 162. When the conductor 68 has been stepped to a position where it is in contact with contact 100, this signal passes through the diode 142 and the conductor 144 to the terminal 146 on the recline/elevate control 148. Positioning of the movable contact 68 into contact with the fixed contact 100 can be considered the wheelchair user recline position and the recline/elevate control 148 will activate reversible recline/elevate control motor 164 in the "recline" direction to move movable portions of the wheelchair into a user recline position. Note that some portions of the wheelchair — for example, leg-rest portions — may actually be elevated in this operation. Hence, the recline/elevate designation refers to the condition of user and not necessarily to the conditions of portions of the wheelchair.

If the user now makes two successive contacts between his skin and the element 30, the stepping switch 64 will be activated twice and the movable contact 68 will be advanced from the "recline" position in which the contact 68 contacts the fixed contact 104. If the user then places his skin in contact with the element 32, the recline/elevate motor 164 will be activated in an "elevate" direction for so long as he keeps his skin in contact with the contact element 38, to move the movable portions of the wheelchair away from the recline position, The "elevate" control signal, which is developed by the amplifier 50 and further amplified by the transistor 158, is supplied through a diode 170 and a conductor 172 to an input terminal 174 on the recline/elevate controller 148. The motion of the recline/elevate motor 164 may be made continuous or intermittent, and the necessary time delays in the activation of drive motors 128 and 130, as the stepping switch 64 advances two positions, can be achieved by utilizing any well-known delay technique, such as delayed action relays or charging capacitors associated with the electrical circuit activating the motors or relays. The circuits for the recline/elevate controller 148 are conventional relay circuits of an electromechanical or solid state variety, and are well-known to those skilled in the art. Positive control voltage is provided through conductor 166 to a terminal 168 on the recline/elevate controller 148.

A control current return path is provided through a terminal 176 and a conductor 178. A protective diode 180 is provided to prevent damage to transistor 58 when the inductive load of stepping switch solenoid 62 is de-energized by transistor 58.

Another way of explaining the operation of the described controlling system is that every other time the switch 64 is stepped, by the user momentarily contacting the element 30, the movable contact 66 is positioned (at contacts 78 or 82) for controlling the speed of the wheelchair drive motors 128 and 130. When the movable contact 66 is in contact with the fixed contact 78, the motors 128 and 130 are selected for "low speed" operation, so that when the "joystick" or other control is actuated, the wheelchair is moved at a low or slow speed. When the movable contact 64 is stepped into contact with the fixed contact 82, the motors 128 and 130 are selected for "high speed" operation; when the "joystick" is then actuated, the wheelchair is moved at a faster speed. At such contact positions 78 or 82 of the movable contact 66, the movable contact 68, which moves in unison therewith, is in contact only with unconnected contacts 98 or 102, and the recline/elevate mechanism cannot be actuated.

When, however, the switch 64 is stepped into intermediate positions, the movable contact 66 contacts unconnected contacts 80 or 84, thereby removing voltage from the motors 128 and 130 (so that the wheelchair cannot be moved) and the movable contact 68 contacts the recline/elevate contacts 100 or 104 to recline or elevate, respectively, the wheelchair user when the user then contacts the pickup element 32.

The stepping switch 64 thereby functions (by element 30) as a two-operation selector switch, additional controlling being required to actually cause propelling of the wheelchair or to cause movable portions thereof to recline or elevate the user. It is emphasized that each user contact with the element 30, irrespective of duration of the contact (assuming that the contact is not extremely short), causes a single contact advancement of the movable contacts 66 and 68. Contrariwise, the duration of user contact with the element 32 determines the extent of reclining or elevating movement of portions of the wheelchair, within pre-established limits. Thus, the element 30 functions generally as a digital switch, whereas the element 32 functions as an analog switch.

In FIG. 2 the conductive foil 26 is shown disposed between a piece of foam rubber or other padding 182 and the front layer 34 of the backrest 28. However, as previously noted, the foil 26 may alternatively be placed elsewhere in the wheelchair where it will be adjacent to major portions of a user's body.

Although there is described hereinbefore a particular motorized wheelchair drive motor and elevate/recline control system, in accordance with the present invention, for purposes of illustrating the manner in which the invention may be used to advantage, it will be appreciated that the invention is not limited thereto.

The described apparatus may be alternatively or also used to enable a wheelchair user to operate such remotely-controlled devices as television, page turners for books, lights, signals for nurses, etc. Additionally, the apparatus may be used in conjunction with other types of control systems operable in other manners to provide a wheelchair user with additional controls and degrees of freedom. In practice, it may be found desirable or convenient to use a switch 64 having greater than two movable contacts or greater than the four fixed contacts associated with each moving contacts 66 and 68. Additional contacts may be utilized for controlling functions other than selecting drive motor speeds or recline/elevate positions, or they may be interconnected in such a manner to perform the above-described functions. If desired, other pickup elements, similar to the elements 30 and 32, and other stepping switches similar to the switch 64, may be included to provide for controlling of other desired functions.

Accordingly, any and all modifications, variations or equivalent arrangements which may occur to those skilled in the art should be considered to be within the scope of the invention as defined in the appended claims.

What is claimd is:

1. In combination with a wheelchair, wheelchair-mounted control apparatus, which comprises:
   a. a periodic energy field source mounted on said wheelchair,
   b. energy field radiating means connected to said source and disposed on said wheelchair in a location to be adjacent to major body portions of an individual using said wheelchair, whereby said energy field may be radiated into the wheelchair user's body,
   c. a field pickup element mounted to said wheelchair and adapted for receiving said energy field from the wheelchair user's body when the user momentarily contacts said element with his exposed skin,
   d. detecting means connected to said element for detecting said energy field received thereby from said wheelchair user, thereby causing detecting means output signals in response to said detected energy field,
   e. at least one function performing means mounted in said wheelchair, and
   f. controlling means connected to said function performing means and said detecting means for controlling operations of said function performing means in response to said detecting means output signals.

2. The invention as claimed in claim 1, wherein said function performing means includes wheelchair propelling means, and wherein said controlling means includes selecting means for enabling selection of at least two different speeds at which said propelling means may be caused to propel said wheelchair.

3. The invention as claimed in claim 2, wherein said selecting means includes stepping switch means having fixed contacts separately connected to select said different speeds, said stepping switch means having a movable stepping contact, movement thereof being responsive to said output signals, a preselected sequence of said output signals causing movement of said movable contact into sequential contact with said fixed contacts to cause said selection of said different speeds.

4. The invention as claimed in claim 1, wherein said function performing means includes reclining and elevating means for causing movement of portions of said wheelchair to enable a user to recline and sit up, and wherein said controlling means includes selecting means for enabling selection of either of recline and elevate modes of operation of said reclining and elevating means.

5. The invention as claimed in claim 4, wherein said selecting means includes stepping switch means having fixed contacts separately connected to select said recline and elevate modes of operation, said stepping switch means having a movable stepping contact, movement thereof being responsive to said output signals, a preselected sequence of said output signals causing movement of said movable contact into sequential contact with said fixed contacts to cause said selection of said recline and elevate modes.

6. The invention as claimed in claim 5, wherein said apparatus further includes a second pickup element mounted to said wheelchair and adapted for receiving said energy field from a wheelchair user's body when the user contacts said second element with his exposed skin, said detecting means being also connected to said second element for detecting said energy field when received thereby from said wheelchair user and for causing second detecting means output signals in response to said detecting energy field received from said second element, said function performing means including means responsive to said second output signals for causing said movement of said wheelchair portions after said stepping switch means has caused selection of either of said recline and elevate modes.

7. The invention as claimed in claim 1, wherein said radiating means comprises a metallic foil disposed within a backrest portion of said wheelchair.

8. The invention as claimed in claim 1, wherein said pickup element is positioned for contacting by neck portions of the wheelchair user.

9. The invention as claimed in claim 1, wherein said field source includes means for varying the periodicity of said field source.

10. A wheelchair control apparatus, which comprises:
    a. a wheelchair,
    b. propelling means mounted on said wheelchair for causing propelling thereof, said propelling means including motor means and means for controlling the power supplied to said motor means and thus to the wheels of said wheelchair, said motor means having selectable first and second drive speeds,
    c. periodic energy field source means mounted on said wheelchair, said sorce means including radiating means disposed on portions of said wheelchair in a location to be proximate to major body portions of an individual using said wheelchair, whereby said energy field from said source means is caused to be radiated into the user's body,
    d. a field pickup element mounted on said wheelchair and adapted for receiving said energy field from a wheelchair user's body when a user momentarily contacts said element with his exposed skin,
    e. detecting means having portions connected to said elements for detecting said energy field when received thereby from said wheelchair user and for causing an output signal in response to said detected energy field, and
    f. selecting means responsive to said output signal for selecting either of said first and second motor speeds in response to a preselected sequence of said output signals, said selecting means including a stepping switch having a first fixed contact connected for selecting said first speed and a second connected for selecting said second speed, and having a movable contact movably responsive to said output signal, a predetermined sequence of said output signals causing movement of said movable contact between said first and second fixed contacts.

11. The invention claimed in claim 10, wherein said wheelchair includes movable portions adapted to enable a user to recline or sit up and means for causing movement of said movable portions, said selecting means including means for selecting in which of recline and elevate modes said means for causing movement will operate.

12. The invention as claimed in claim 11, wherein said recline and elevate mode selecting means includes a second portion of said stepping switch having a first fixed contact connected for selecting said recline mode and a second fixed contact connected for selecting said elevate mode, and having a second movable contact connected to move in unison with said first-mentioned movable contact, said predetermined sequence of said output signals also causing movement of said second movable contact between said first and second contacts of said second portion.

13. The invention as claimed in claim 12, wherein said first and second fixed contacts of said first-mentioned portion of said stepping switch and said first and second fixed contacts of said second portion of said stepping switch are staggered, whereby said preselected sequence of said output signals causes selection, in sequence of: said first motor speed, said recline mode, said second motor speed, and said elevated mode.

14. The invention as claimed in claim 11, wherein said means for causing movement of said movable portions includes a second field pickup similar to said first-mentioned pickup element and adapted for receiving said energy field from a wheelchair user's body when the user contacts said second element with his exposed skin, said detecting means having a second portion connected to said second element for detecting said energy field received thereby from said wheelchair user and for causing a second output signal in response to said detected energy field, the duration of said second output signal corresponding to the length of skin contact with said second element by the user, whereby, within predetermined limits, when either of said recline and elevate modes has been selected, movement of said movable portions continues as long as the user maintains his exposed skin in contact with said second element.

* * * * *